(12) United States Patent
Oroskar et al.

(10) Patent No.: US 9,163,050 B2
(45) Date of Patent: Oct. 20, 2015

(54) MANNOSE PRODUCTION FROM PALM KERNEL MEAL USING SIMULATED MOVING BED SEPARATION

(75) Inventors: Anil R Oroskar, Oak Brook, IL (US); Naveen S Sudharsan, Downers Grove, IL (US); Priyanka Anil Oroskar, Oak Brook, IL (US); Omkar M Kulkarni, Naperville, IL (US)

(73) Assignee: OROCHEM TECHNOLOGIES, INC., Naperville, IL (US)

( * ) Notice: Subject to any disclaimer, the term of this patent is extended or adjusted under 35 U.S.C. 154(b) by 450 days.

(21) Appl. No.: 13/567,447

(22) Filed: Aug. 6, 2012

(65) Prior Publication Data

US 2014/0039180 A1 Feb. 6, 2014

(51) Int. Cl.
*B01D 15/18* (2006.01)
*B01J 39/08* (2006.01)
(Continued)

(52) U.S. Cl.
CPC .. *C07H 3/02* (2013.01); *B01D 1/26* (2013.01); *B01D 15/185* (2013.01);
(Continued)

(58) Field of Classification Search
CPC .............. B01D 1/00; B01D 1/26; B01D 9/00; B01D 9/0018; B01D 9/0031; B01D 9/0045; B01D 15/08; B01D 15/12; B01D 15/125; B01D 15/20; B01D 15/36; B01D 15/362; B01D 15/363; B01D 15/1821; B01D 15/1828; B01D 15/1835; B01D 15/185; B01D 2215/023; B01D 2215/021; B01D 61/58; B01D 2311/04; B01D 2311/06; B01D 2311/2673; B01D 2311/2623; B01D 2311/2626; B01D 2311/2642; B01J 20/34; B01J 20/3071; B01J 39/00; B01J 39/02; B01J 39/08; B01J 39/085; B01J 41/00; B01J 41/02; B01J 41/10; B01J 41/20; B01J 43/00; B01J 47/02; B01J 49/00; B01J 49/004; B01J 19/0008; B01J 49/0017; B01J 49/0013; B01J 49/0091; B01J 39/043; B01J 47/026; B01J 49/003; B01J 49/0026; B01J 49/0034; C07H 1/06; C07H 1/08; C07H 3/02; C13K 1/00; C13K 1/10; C13K 7/00; C13K 13/007; C12P 19/02
USPC .............. 127/46.1, 46.2, 46.3, 53, 55, 58, 61; 159/17.1, 47.1; 203/29, 32, 38, 39, 41, 203/47, 48, 71, 81, 91; 210/651, 652, 659, 210/662, 663, 669, 675, 676, 679, 681, 683, 210/685, 690, 702, 774, 806, 770, 805; 435/276; 536/128
See application file for complete search history.

(56) References Cited

U.S. PATENT DOCUMENTS 2,985,589 A 5/1961 Broughton
4,359,430 A 11/1982 Heikkila
(Continued)

OTHER PUBLICATIONS

Fredrick J. Bates & Associates, "Polarimetry, Saccharimetry and the Sugars", May 1, 1942, pp. 632-636, Circular of the National Bureau of Standards C440, Washington, D.C.
(Continued)

*Primary Examiner* — Joseph Drodge
(74) *Attorney, Agent, or Firm* — Richard P. Silverman & Assoc., LLC

(57) ABSTRACT

Disclosed is a process for the production of d-mannose from fermented palm oil kernel meal using a continuous SMB separation process. The process is useful for providing a simplified processing route to providing high purity d-mannose. The SMB process and the SMB cycle was operated to provide a high purity mannose stream comprising d-mannose, salts, and color agents, a primary raffinate comprising glucose, other sugars and salts, and a secondary raffinate consisting essentially of the mobile phase desorbent. In the SMB cycle, the secondary raffinate was recycled to the SMB process as the mobile phase desorbent without further desalination. The highly pure mannose stream was further treated to remove color agents and salts prior to subsequent steps of precipitation or crystallization and drying. D-mannose is useful as a food additive, as a sweetener, as a texturizer, as a stabilizer, or as a humectant.

20 Claims, 3 Drawing Sheets

(51) Int. Cl.
| | |
|---|---|
| *B01J 47/02* | (2006.01) |
| *B01J 49/00* | (2006.01) |
| *B01D 61/58* | (2006.01) |
| *C07H 3/02* | (2006.01) |
| *C07H 1/08* | (2006.01) |
| *C13K 1/10* | (2006.01) |
| *C13K 7/00* | (2006.01) |
| *B01D 1/26* | (2006.01) |
| *C12P 19/02* | (2006.01) |
| *C13K 13/00* | (2006.01) |
| *B01D 15/36* | (2006.01) |
| *B01J 39/04* | (2006.01) |

(52) U.S. Cl.
CPC .......... *B01D 15/1821* (2013.01); *B01D 15/362* (2013.01); *B01D 61/58* (2013.01); *B01J 39/043* (2013.01); *B01J 47/026* (2013.01); *B01J 49/003* (2013.01); *C07H 1/08* (2013.01); *C13K 1/10* (2013.01); *C13K 7/00* (2013.01); *C13K 13/007* (2013.01); *B01D 2311/2623* (2013.01); *B01D 2311/2673* (2013.01); *C12P 19/02* (2013.01)

(56) References Cited

U.S. PATENT DOCUMENTS

| | | | |
|---|---|---|---|
| 4,412,866 A | 11/1983 | Schoenrock | |
| 4,880,920 A | 11/1989 | Chang | |
| 5,002,612 A | 3/1991 | Beadle | |
| 5,008,189 A | 4/1991 | Oroskar | |
| 5,102,553 A | 4/1992 | Kearney | |
| 5,176,832 A | 1/1993 | Dorta | |
| 5,466,294 A | 11/1995 | Kearney | |
| 6,057,135 A | 5/2000 | Ibrahim | |
| 6,093,326 A | 7/2000 | Heikkilaeet | |
| 6,187,204 B1 | 2/2001 | Heikkilaeet | |
| 6,379,554 B1 | 4/2002 | Kearney | |
| 6,451,123 B1 | 9/2002 | Saska | |
| 6,872,314 B2 * | 3/2005 | Boyd et al. | 210/635 |
| 6,896,811 B2 | 5/2005 | Heikkilaeet | |
| 6,896,918 B2 | 5/2005 | Yokomizo | |
| 6,911,565 B2 | 6/2005 | Heikkilaeet | |
| 7,722,721 B2 | 5/2010 | Heikkilaeet | |
| 7,931,751 B2 | 4/2011 | Costesso | |
| 2003/0222021 A1 | 12/2003 | Ennelin | |
| 2004/0006223 A1 * | 1/2004 | Karki et al. | 536/124 |
| 2004/0151804 A1 * | 8/2004 | Yokomizo | 426/44 |
| 2005/0161401 A1 * | 7/2005 | Heikkila et al. | 210/656 |
| 2005/0188912 A1 | 9/2005 | Unno | |
| 2009/0198088 A1 * | 8/2009 | Tirio et al. | 568/870 |
| 2010/0234587 A1 | 9/2010 | Vagnoli | |
| 2012/0279497 A1 * | 11/2012 | Jansen et al. | 127/29 |
| 2013/0052682 A1 * | 2/2013 | Medoff et al. | 435/68.1 |

OTHER PUBLICATIONS

Tang Thin Sue, Quality and Characteristics of Malaysian Palm Kernel Cakes/Expellers, (1985) pp. 1-3, Palm Oil Developments 34, Available online at http://palmoilis.mpob.gov.my/publications/pod34-tang.pdf, Malaysian Palm Oil Board, Kuala Lumpur, Malaysia.

Saenphoom, P., J. B. Liang, Y. W. Ho, T. C. Loh, M. Rosfarizan, "Effect of enzyme treatment on chemical composition and production of reducing sugars in palm (*Elaeis guineenis*) kernel expeller", African Journal of Biotechnology vol. 10 (68), pp. 15372-15377, Nov. 2, 2011, Available online at http://www.academicjournals.org/AJB.

* cited by examiner

MANNOSE PRODUCTION FROM PALM KERNEL MEAL USING SIMULATED MOVING BED SEPARATION

FIELD OF THE INVENTION

This invention concerns generally with a process for the production of d-mannose from palm kernel meal (PKM), a byproduct of the production of palm oil. More particularly, it relates to a process for the recovery of d-mannose from a mixture of saccharides and the use of a simplified separation scheme based on simulated moving bed (SMB) separation. Further, it relates to the use of a solvent precipitation step to further purify the d-mannose or a crystallization step for the recovery of high purity mannose.

BACKGROUND

D-mannose is a sugar monomer of the aldohexose series of carbohydrates. D-mannose is a C-2 epimer of glucose, and has the following structure:

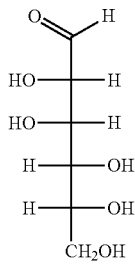

D-mannose is important in human metabolism, especially in the glycosylation of certain proteins.

The Palm kernel is the edible fruit of the oil palm tree. It yields two distinct oils—palm oil and palm kernel oil. The pulp left after oil is rendered is formed into "palm kernel cake", and is typically used either as high-protein feed for dairy cattle or burned in boilers to generate electricity for palm oil mills. A byproduct which is produced in conjunction with the production of palm oil is palm kernel cake (PKC), which is sometimes referred to as either palm kernel meal (PKM) or palm kernel expeller (PKE) depending upon the method employed in the extraction of the oil from the palm kernel. The process for producing the palm kernel cake is described in an article by Tang Thin Sue, entitled, "Quality and Characteristics of Malaysian Palm Kernel Cakes/Expellers." In general, the PKE byproduct is produced by a screw-pressing and filtration process, rather than a higher cost solvent extraction process.

The PKC or PKE contains a moderate level of crude protein (14.5 to 19.6 percent), but a high level of fiber (13-20 percent) and a poor amino acid profile which is deficient in lysine, methionine and tryptophan, and as such is considered a moderate quality food for ruminant mammals (having two-stomachs, such as cows) and not suitable for monogastric animals. The fiber of the PKE is primarily hemicelluloses consisting of mannans, moderate amounts of cellulose and small amounts of polysaccharides. The mannan portion of the PKE can range from between 25 to 32 percent. Because the mannan is hard and water insoluble and has a complex chemical structure, a combination of enzymes including mannosidases, galactosidases, glucosidases, and xylanases are required to release the potential fermentable sugars to improve the nutritive value of PKE to be of use to monogastric animals. Enzyme treatment of PKE for the improvement of the nutritive value of PKE is further described in an article by Saenphoom, et al., entitled, "Effect of enzyme treatment on Chemical composition and production of Reducing Sugars in Palm (*Elaeis guineenis*) Kernel Expeller."

U.S. Pat. No. 6,896,918 discloses a mannose containing palm kernel meal can be obtained by reacting a mannan degrading enzyme or an acid catalyst with palm kernel meal. A mixture of palm kernel meal, a mannan degrading enzyme and water thus prepared is reacted at the optimal temperature for the enzymatic activity to effect the reaction, and a wet composition is obtained. Mannose or mannosides (mannobiose, mannotriose, and mannooligosaccharides) are generated with the amounts depending on the reaction time in the wet composition. When the reaction time is between 24 to 72 hours, up to about 10-25 parts by weight of mannose are produced per 100 parts by weight of the material palm kernel meal, depending upon the amount of enzyme used. The resulting wet product, without further water removal, can be used as a feedstuff additive for preventing Salmonella infection. The palm kernel meal after the enzyme reaction contains considerable amount of water and the development of mold and fungi can occur during distribution and use, if untreated. In which case, the wet palm kernel meal may be dried to a water content of equal to or less than 10% by methods such as fluidized-bed drying or the like. Further, when highly purified mannose is required as materials for fine chemicals, it may be extracted and purified with an adequate catalyst such as water etc.

Simulation of a moving sorbent bed is described in U.S. Pat. No. 2,985,589 (Broughton et al.), which is mentioned above. In accomplishing this simulation, it is necessary to connect a feedstream to a series of beds in sequence, first to bed no. 1, then to bed no. 2, and so forth for numerous beds, the number of beds often being between 12 and 24. These beds may be considered to be portions of a single large bed whose movement is simulated. Each time the feedstream destination is changed, it is also necessary to change the destinations (or origins) of at least three other streams, which may be streams entering the beds, such as the feedstream, or leaving the beds. The moving bed simulation may be imply described as dividing the bed into series of fixed beds and moving the points of introducing and withdrawing liquid streams past the series of fixed beds instead of moving the beds past the introduction and withdrawal points. A rotary valve used in the Broughton process may be described as accomplishing the simultaneous interconnection of two separate groups of conduits.

U.S. Pat. No. 4,412,866 describes an example of the operation of chromatographic simulated moving bed (or sometimes called "SMB") method to separate the components of a feed stock. A resin bed is divided into a series of discrete vessels, each of which functions as a zone within a circulation loop. A manifold system connects the vessels and directs, in appropriate sequence to (or from) each vessel, each of the four media accommodated by the process. Those media are generally referred to as feed stock, eluent, extract and raffinate, respectively. As applied to a sugar factory, a typical feed stock is a lower purity sucrose solution, the eluent is water, the extract is an aqueous solution of sucrose and the raffinate is an aqueous solution containing non-sucrose, such as salts and high molecular weight compounds. The simulated moving bed disclosed by the '866 patent is of the type sometimes referred to as a "continuous SMB."

An example of a batch chromatographic method for the purification of sucrose is described in the disclosure of U.S. Pat. No. 4,359,430, which utilizes sucrose feedstocks derived from sugar beets at purities of approximately 7% to 60% sucrose. See also, e.g., U.S. Pat. No. 5,466,294, which utilizes a "soft raw syrup" as a feedstock to a chromatographic method which is not in a high purity form at a less than 89% purity sucrose on a dry solids basis, i.e., approximately 11% non-sucrose impurities.

US Patent Publication US2003/0222021 discloses a chromatographic separation process for recovering mannose with high purity using a chromatographic separation including a resin which is at least partially in a $Ba^{2+}$ form resin and a resin which is other than $Ba^{2+}$ form.

Methods are sought for a more efficient method of producing d-mannose from palm kernel meal.

SUMMARY OF THE INVENTION

Applicant's invention relates to the production of mannose from palm kernel meal (PKM), a byproduct of the production of palm oil. Palm kernel meal is typically a wet product. Without further drying of the palm kernel meal, applicant discovered that high purity d-mannose can be efficiently produced by the combination comprising a biomass removal step, a selective continuous simulated moving bed (SMB) process, a decolorization step, a desalination step, and a crystallization step. The feedstock which is charged to the SMB is the fermented palm oil kernel in the form of an aqueous syrup. Following filtration, the feedstock is processed in the SMB to provide an extract stream comprising d-mannose, a first raffinate stream comprising impurities, and a second raffinate stream comprising the mobile phase desorbent essentially free of salts. The extract stream, comprises high purity d-mannose, having a purity of about 95 wt-% d-mannose. The extract stream is then subjected to decolorization, desalination, precipitation, crystallization and drying to provide a d-mannose product which can be granular or a powder, having a purity greater than or equal to 99 wt-% d-mannose.

In one embodiment, the present invention is a process for the production of a high purity d-mannose product from fermented palm oil kernel meal using simulated moving bed separation. The process comprises passing a palm kernel meal stream comprising water, d-mannose, d-glucose, other sugars, color agents, salts and biomass to a filtration zone. The filtration zone has a filter media effective to remove at least a portion of the biomass to provide a filtered feedstream comprising water, d-mannose, d-glucose, salts, and other sugars The filtered feedstream at a pH of between about 4 and about 6 is passed to a simulated moving bed (SMB) zone to provide a highly pure mannose stream comprising d-mannose, color agents, salts and water, and a primary raffinate stream comprising water, d-glucose, salts, and other sugars, and a secondary raffinate stream consisting essentially of water. The SMB zone comprises a plurality of adsorption beds containing a stationary phase agent comprising an effective ion exchanged resin. A mobile phase stream comprising water is introduced to the SMB zone. The SMB zone is operated at effective conditions and is operated in an effective SMB cycle including rectification, adsorption, and regeneration to provide a continuous process for producing the highly pure mannose stream. At least a portion of the secondary raffinate stream is returned to the SMB zone to be admixed with the mobile phase stream. The highly pure mannose stream is passed to a decolorization zone wherein the highly pure mannose stream is contacted with a medium effective to at least partially remove the color agents to provide a decolorized stream comprising d-mannose, salts and water. The decolorized stream is passed to a first evaporation zone to remove at least a portion of the water and provide a first evaporated stream. The first evaporated stream is passed to a desalination zone to provide a desalinized stream. The desalinized stream is passed to a second evaporation zone to provide an evaporated desalinized stream. The evaporated desalinized stream is passed to a precipitation zone or a crystallization zone to provide a wet mannose crystal stream; and, the wet mannose crystal stream is passed to a vacuum drying zone to provide the high purity d-mannose product.

BRIEF DESCRIPTION OF THE DRAWINGS

The following drawings are illustrative of the embodiments of the invention and are not meant to limit the scope of the invention in any way.

DETAILED DESCRIPTION OF THE INVENTION

Feedstock

Figure 1:
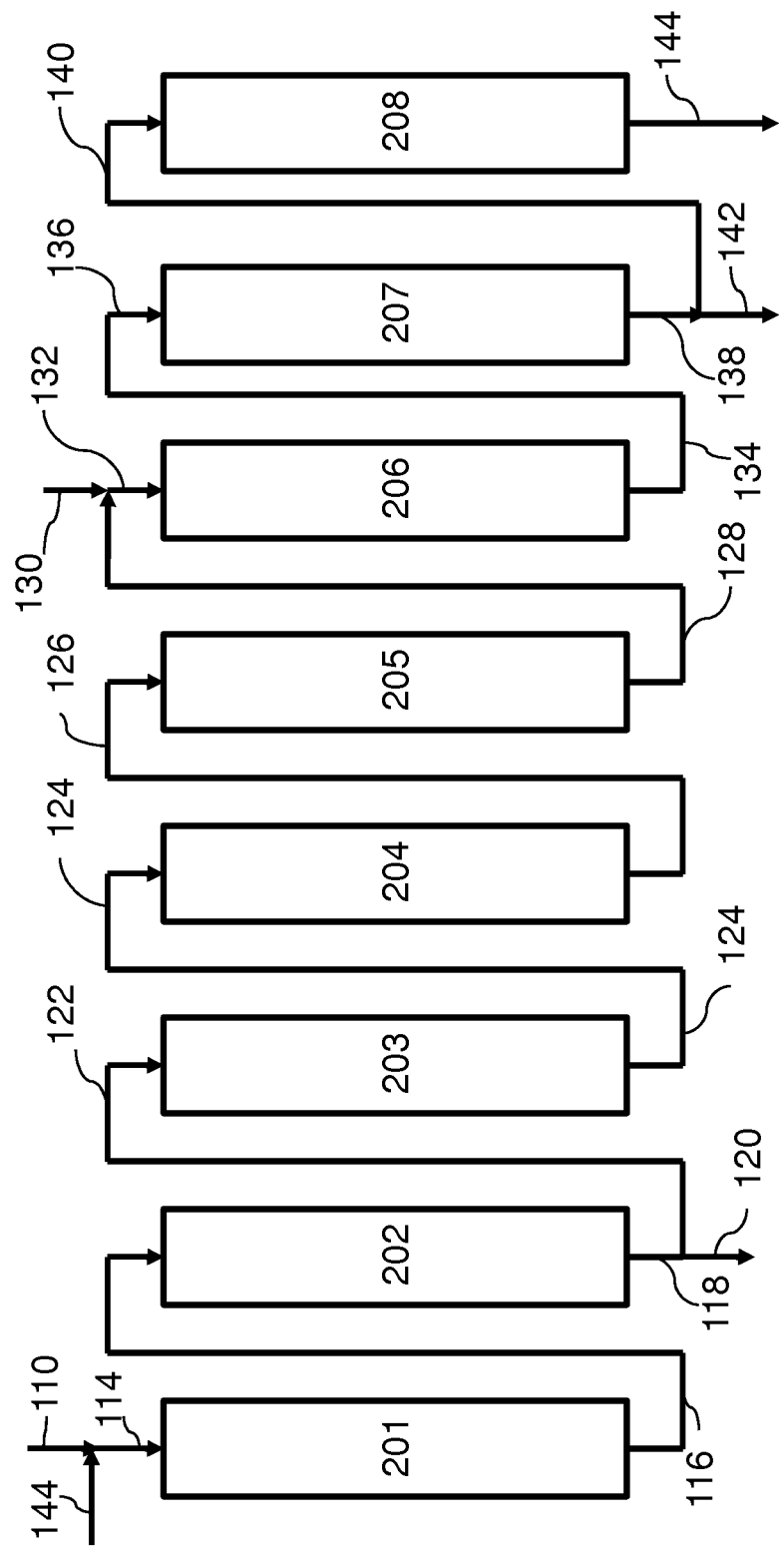
FIG. 1 is a schematic process flow diagram representing one embodiment of the present invention for a basic simulated moving bed adsorption process employing eight adsorption beds.

The feedstock for the SMB zone is a fermentation product of the enzymatic fermentation of palm oil kernel. The feedstream is typically a wet composition comprising water, mannose or mannosides (mannobiose, mannotriose, mannooligosaccharides), and dissolved biomass. The feedstream typically has a density of about 14 Brix (A measurement of the dissolved sugar-to-water mass ratio of a liquid, where 20 Brix is equivalent to 20 grams of sugar in 80 grams of water) and comprises about 60 to 70 wt-% d-mannose. The fermentation which produced the feedstream was typically carried out at a pH of between 4 and 5. Prior to introducing the feedstream to the SMB zone, the feedstock was filtered in an ultra-filtration zone over a filter media, wherein the filter media is a membrane having a molecular weight cut off of at least a 70 kDa (70,000 Daltons) to remove at least a portion of the biomass, and preferably essentially all of the biomass. More preferably, the filter media is a membrane having a molecular weight cut off of between about 10 kDa to about 70 kDa. Most preferably, the filter media is a membrane having a molecular weight cut off of less than or equal to a 10 kDa. Generally, one skilled in the art of adsorbent separation would be motivated to remove any soluble biomass prior to processing the feedstock in the SMB process. It is generally believed that retaining any biomass in the feedstock to the SMB would result in premature failure due to plugging or higher than acceptable pressure drops in the adsorbent zones. However, it was surprisingly discovered that it was critical not to attempt to remove the soluble biomass from the feedstock prior to the SMB zone using a denaturation step with a solvent. Typically, removal of the soluble biomass is performed by contacting the feedstock with a solvent such as ethanol, acetonitrile, and chloroform, or by the introduction of strong acids such as trichloro acetic acid in a biomass extraction or naturation step. It was found that the presence of solvent in any amount in the feedstream will result in solvent accumulating in the SMB mobile phase stream or desorbent, which will degrade the operation of the SMB zone. Ultra-filtration of the feedstream to remove the biomass prior to the SMB zone, or optionally, denaturation of the extract stream (highly pure d-mannose stream) following separation in the SMB zone avoids the need for a significant amount of capital equipment and the significantly increased operating costs to affect the removal of solvents from the mobile phase stream.

The SMB system of the current invention was arranged for maximum selectivity. The simulated moving bed operation is achieved by use of a plurality of adsorbent beds connected in series and a complex valve system, whereby the complex valve system facilitates switching at regular intervals the feed entry in one direction, the mobile phase desorbent entry in the opposite direction, while changing the extract and raffinate takeoff positions as well. The SMB system is a continuous process. Feed enters and extract and raffinate streams are withdrawn continuously at substantially constant compositions. The overall operation is equivalent in performance to an operation wherein the fluid and solid are contacted in a continuous countercurrent manner, without the actual movement of the solid, or stationary phase adsorbent.

The operation of the SMB system is carried out at a constant temperature within the adsorbent bed. Preferably, the SMB zones of the present invention operate at an SMB temperature of about 50° C. to about 65° C. More preferably, the SMB zones of the present invention operate at an SMB temperature of between about 55° C. to about 60° C. The feedstream is passed to the SMB zone at a pH of from about 4 to about 6. More preferably, the feedstream is passed to the SMB zone at a pH of from about 4.5 to about 5. The feedstream is introduced and components are adsorbed and separated from each other within the adsorbent bed. A separate liquid, the mobile phase desorbent, is used to counter currently displace the feed components from the pores of the stationary phase adsorbent. During the SMB cycle of the present invention, adsorbent beds are advanced through a desorption zone, a rectification zone, an adsorption zone, and a regeneration zone. The description of the SMB cycle as a 2-3-2-1 cycle means that in the cycle, 2 adsorbent beds are in the desorption zone, 3 adsorbent beds are in the rectification zone, 2 adsorbent beds are in the adsorption zone, and a single bed is reserved for the mobile phase stream or desorbent recycle.

The adsorbents of the present invention have been found to be effective for the adsorption of mannose selectively over glucose. In addition, it has also been found that the initial performance of the effective adsorbent is maintained during the actual use in the separation process over an economically desirable life. In addition, as previously set forth, the effective adsorbent of the instant invention possesses the ability to separate components of the feed; that is, that the effective adsorbent possesses adsorptive selectivity for one component as compared to other components. The adsorbents used in the separation of this invention are effective ion exchange resins in which the resin is a strong cation acid resin and the exchange sites are Group I and/or Group II metals such as $Ca^{2+}$, $Na^+$ and $K^+$. The following table shows the relative selectivity of some of these effective adsorbents for the adsorption of mannose over other sugars:

| Sugar | Relative Selectivities | | |
| --- | --- | --- | --- |
| | $Ca^{2+}$ | $Na^+$ | $K^+$ |
| Glucose | 2.74 | 2.3 | 2.2 |
| Xylose | 3.07 | 2.8 | 2.7 |
| Galactose | 1.47 | 1.3 | 1.3 |
| Mannose | 1.0 | 1.0 | 1.0 |
| Arabinose | 1.32 | 1.2 | 1.2 |

Preferably, the stationary phase adsorbents used in the separation of this invention are the strong acid cation exchange resins in which the exchange sites are calcium ions ($Ca^{2+}$). The resins may be made by the process described in U.S. Pat. No. 4,444,961, which provides very uniform spherical size polymeric beads. Preferably, the stationary phase adsorbent will have an average particle size of from 220 microns to about 350 microns and the resin will have a cross link percentage of from about 4 to about 8 percent. More preferably, the stationary phase adsorbent will have an average particle size of from 220 microns to about 350 microns and the resin will have a cross link percentage of from about 6 to about 8 percent. U.S. Pat. No. 4,444,961 is hereby incorporated in its entirety by reference. In some cases, the resin may be available in the hydrogen form, and the resin may be exchanged with $Ca^{2+}$ or $Na^+$ or $K^+$ ions. Alternatively, the resin may be exchanged with multiple ions in a single solution in a ratio calculated or experimentally determined to exchange the respective ions in the desired ratio. Exchange methods are well known to those of ordinary skill in the art and are suitable for the resins of this invention. The preferred SMB stationary phase desorbent in the SMB zone is a strong acid cation calcium exchange resin such as DOWEX 99CA/320 (Available from The Dow Chemical Company, Midland, Mich.), or other such resins as Rohm and Haas 1310 and 1320 resins, PUROLITE PCR resins (Available from Purolite, Bala Cynwyd, Pa.), and other DOWEX monosphere chromatographic resins. Other such resins include UBK555 (Mitsubishi Chemical Co., Carmel Ind.).

DETAILED DESCRIPTION OF THE DRAWINGS

FIG. 1 shows one embodiment of the simulated moving bed SMB adsorption zone of the present invention based on an eight adsorbent bed arrangement. Adsorbent beds 201, 202, 203, 204, 205, 206, 207, and 208, containing a stationary phase adsorbent comprising an effective ion exchanged acid resin, are disposed in a serial configuration such that in accordance with a prearranged cycle, conduit 116 provides fluid communication between the bottom of adsorbent bed 201 with the top of adsorbent bed 202, conduits 118 and 122 provide fluid communication between the bottom of adsorbent bed 202 bed and the top of adsorbent bed 203, conduit 124 provides fluid communication between the bottom of adsorbent bed 203 with the top of adsorbent bed 204, conduit 126 provides fluid communication between the bottom of adsorbent bed 204 with the top of adsorbent bed 205, conduits 128 and 132 provide fluid communication between the bottom of adsorbent bed 205 with the top of adsorbent bed 206, conduit 134 provides fluid communication between the bottom of adsorbent bed 206 with the top of adsorbent bed 207, conduits 138 and 140 provide fluid communication between the bottom of adsorbent bed 207 and the top of adsorbent bed 208. The mobile phase is introduced in conduit 110; the extract is withdrawn from adsorbent bed 202 via conduits 118 and 120; a primary raffinate stream is withdrawn from adsorbent bed 207 via lines 138 and 142; and, a secondary raffinate is withdrawn from the bottom of adsorbent bed 207 via conduit 142. According to the prearranged SMB cycle of the present invention, an SMB zone feedstream is passed to the SMB adsorption zone in line 130 and 134 to adsorbent bed 206. A desorbent stream, or mobile phase stream, comprising water is introduced to adsorbent bed 201 via conduits 110 and 114. A primary raffinate stream is withdrawn from adsorbent bed 207 in conduits 138 and 142, and an extract stream is withdrawn via conduits 118 and 120 from adsorbent bed 202. A secondary raffinate stream consisting essentially of water is withdrawn from adsorbent bed 208 in line 144. Although not shown in FIG. 1, all or at least a portion of the secondary raffinate stream in line 144 is returned to the SMB zone to be admixed with the mobile phase stream in conduits 110 and 114, wherein a makeup mobile phase stream in conduit 110 is admixed with the secondary raffinate stream in conduit 144, prior to introducing the mobile phase stream to adsorbent bed 201. The recycle of the secondary raffinate stream to be used as a portion of the mobile phase desorbent is possible because the SMB cycle is arranged to provide the range of the secondary raffinate flow rate to be equal to the void volume of the last adsorbent bed in order to retain essentially all of the salts in the last adsorbent bed in the SMB sequence. In this manner the secondary raffinate stream will consist essentially of water, the mobile phase desorbent. As described hereinabove, in the SMB cycle, the adsorbent beds 201-208 are indexed according to a 2-3-2-1 SMB cycle such that at least 2 adsorbent beds (201 and 202) undergo desorption, at least 3 adsorbent beds (203, 204, and 205) undergo rectification, and at least 3 adsorbent beds (206, 207) undergo adsorption and a single bed 208 is operated to provide a secondary raffinate stream in conduit 144 having a reduced amount of salt relative to the primary raffinate and essentially no sugars.

Figure 2:
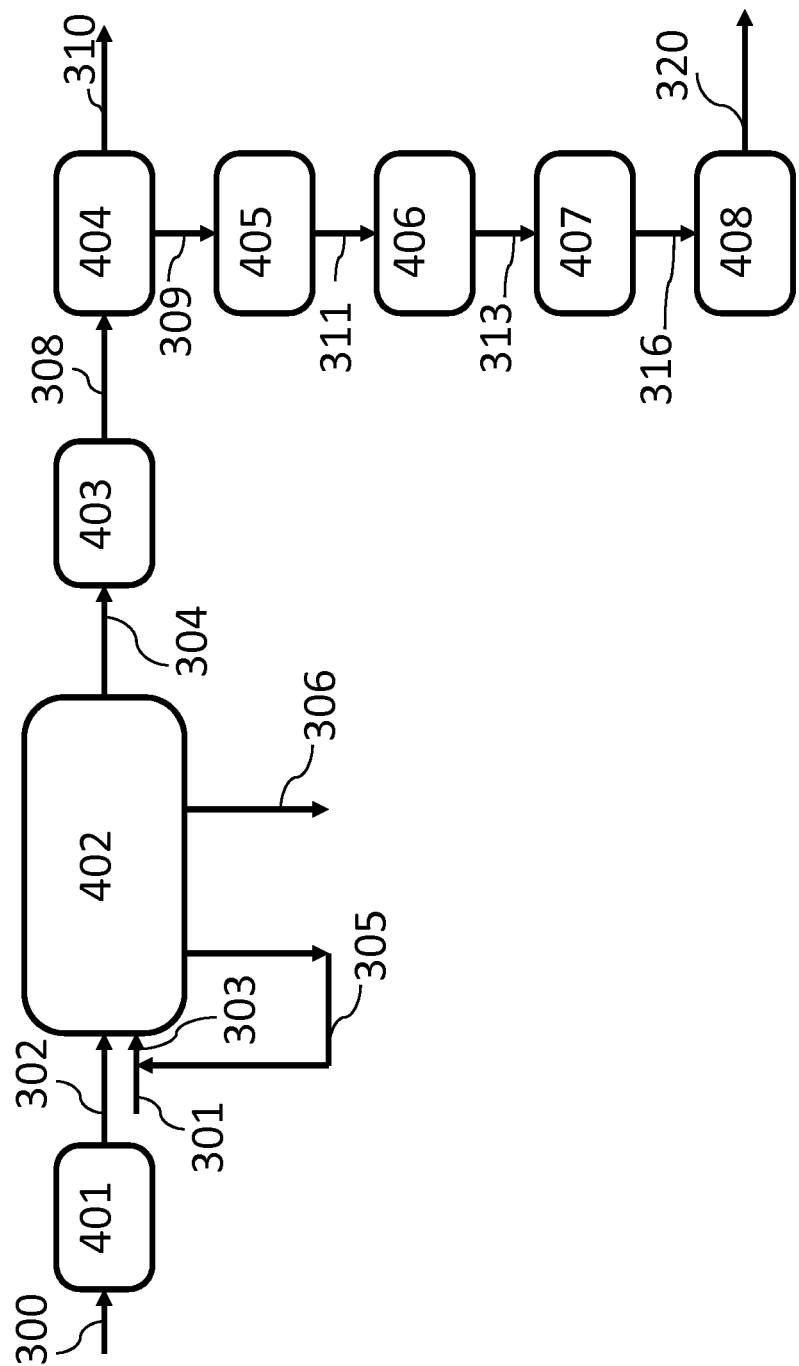
FIG. 2 is a schematic flow diagram one embodiment of the invention illustrating the operation of a d-mannose production scheme employing a selective SMB zone, a biomass removal zone, and a d-mannose crystallizer.
Figure 3:
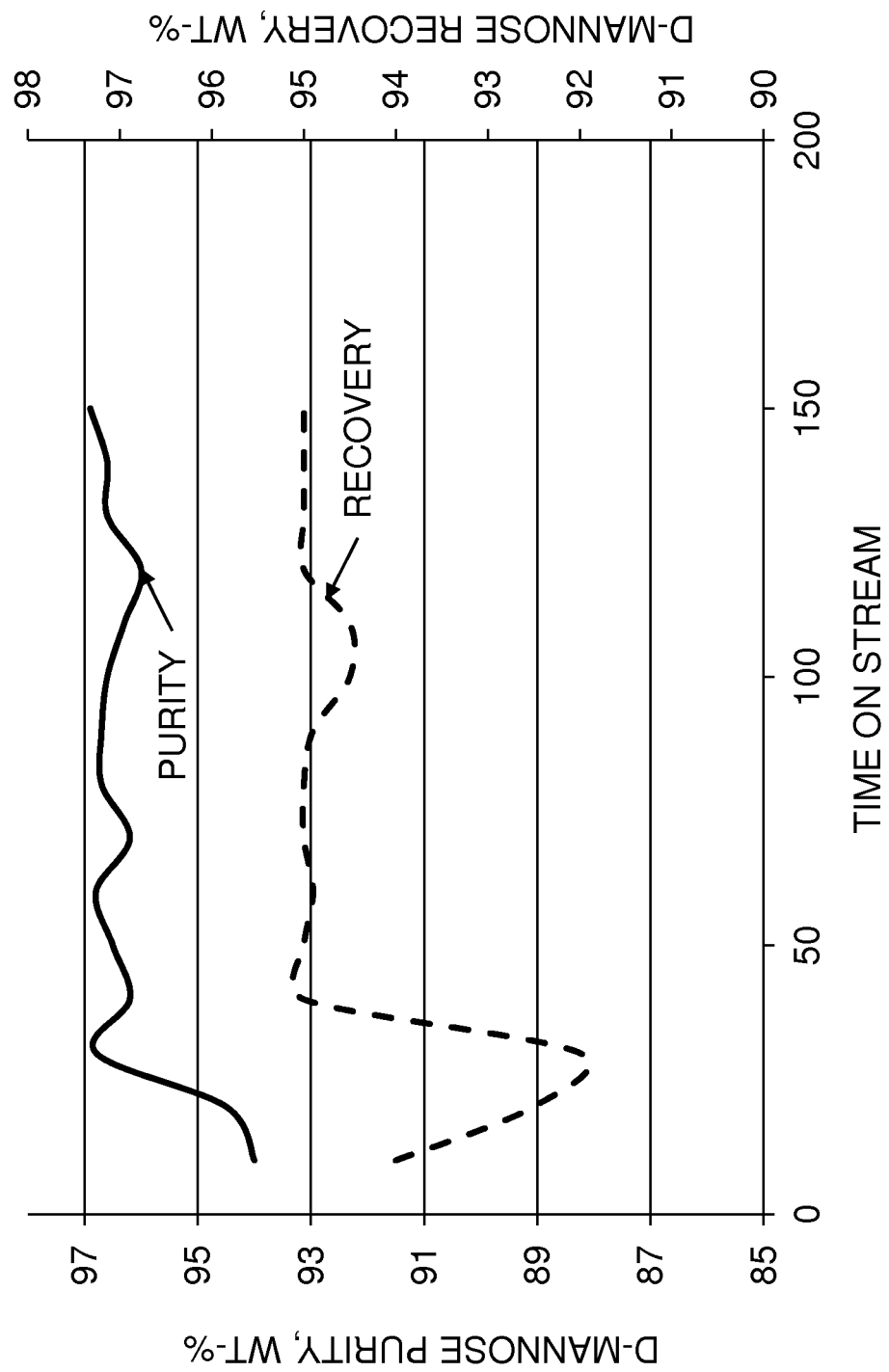
FIG. 3 is a graphical representation of the purity and the recovery of d-mannose as a function of time for a continuous SMB process embodiment of the present invention.

According to an embodiment of the invention and with reference to FIG. 2, a feedstream derived from the fermentation of palm oil kernel as a mixture of palm kernel meal in water and comprising biomass, d-mannose, d-glucose, other sugars, color agents, salts and water in line 300 is passed to a filtration zone 401. As used herein the term soluble biomass includes biomass, proteins and other soluble impurities. While maintaining the pH of the feedstream at a pH of between about 4 and 6, and more preferably maintaining the pH of the feedstream at a pH of between about 4.5 and about 5.0, the feed steam is filtered to provide a filtered feedstream in line 302 having a Brix value of from about 10 to 15. In the filtration zone 401, the feedstream is filtered through a filter media effective to remove at least a portion of the biomass to provide a filtered feedstream comprising water, d-mannose, d-glucose, other sugars, color agents and salt in line 302. Preferably, the filtered feedstream comprises less than about 0.05 wt-% biomass, and more preferably, the filtered feedstream comprises less than about 0.005 wt-% biomass. The filtered feedstock in line 302 is passed to an SMB zone 402 containing at least 8 adsorbent beds containing a strong acid cation calcium exchange resin and operating a 2-3-2-1 cycle as described in FIG. 1. A makeup mobile phase desorbent stream in line 301 is passed to the SMB zone via lines 301 and 303. The mobile phase desorbent in line 301 comprising water is admixed with a secondary raffinate stream in line 305 consisting essentially of water produced in the SMB zone prior to introducing the mobile phase desorbent stream in line 303 to the SMB zone 402. The SMB zone 402 is operated as described hereinabove to provide a primary raffinate stream in line 306 and an extract stream, or highly pure mannose stream comprising water, d-mannose, other sugars, salts, and color agents in line 304, and the secondary raffinate stream in line 306. The primary raffinate stream in line 306 comprises d-glucose, other sugars, salts and water and can be passed to further processing for recovery of other sugars or passed to waste water disposal. The extract stream or highly pure mannose stream in line 304 is of high purity and comprises d-mannose having a purity of greater than about 95 wt-% d-mannose at a recovery greater than about 90 wt-% based on sugars. The highly pure mannose stream in line 304 still comprises color agents and salts which must be removed to provide a highly pure form of d-mannose product. Accordingly, the highly pure mannose stream in line 304 is passed to a decolorizing zone 403 wherein the extract stream in line 304 is contacted with an adsorbent or absorbent selective for the effective removal of the color agents. The adsorbent or absorbent effective for the removal of color agents for example is a granular activated carbon adsorbent to adsorb color agents and provide a decolorized stream in line 308 which comprises water, d-mannose, other sugars, and salts. The decolorized stream in line 308 is passed to a first evaporization zone 404 to remove at reduced pressure at least a portion of the water from the decolorized stream to provide an evaporated decolorized stream, or first evaporated stream in line 309 having a Brix of about 30. The first evaporation stream in line 309 is passed to a desalination zone 405 wherein the first evaporated stream in line 309 is first contacted with a strong anion exchange resin such as a styrene-divinylbenzene gel with 8% cross linkage, for example: DOWEX 1×8 200-400 MESH CI (Available from The Dow Chemical Company, Midland, Mich.), and contacting the resulting effluent with a strong cation exchange resin such as a styrene-divinylbenzene gel with a 4% cross linkage, for example: DOWEX 50WX4-400 (Available from The Dow Chemical Company, Midland, Mich.) to reduce or remove salt from the first evaporation stream in line 309 to provide a desalinized stream in line 311. The desalinized stream in line 311 has a salt content of less than about 50 ppm-wt. The desalinized stream in line 311 is passed to a second evaporization zone 406 and therein evaporated at reduced pressure to provide a second evaporation stream in line 313 having a Brix of from about 90 to about 95. The second evaporation stream in line 313 is passed to a precipitation zone or a crystallization zone show herein as block 407 wherein the second evaporation stream comprising high purity d-mannose is precipitated with ethanol or alternatively crystallized with acetic acid to provide a wet mannose crystal product in line 316. The wet mannose crystal product is passed to a vacuum drying zone 408 to provide a high purity d-mannose product 320. The high purity d-mannose product can be granular or a powder having a purity greater than or equal to 99 wt-%.

The SMB zone may be operated such that the adsorbent beds are operated individually or in parallel using a single rotary valve and associated control system. The circuit is arranged in a 2-3-2-1 configuration, as described hereinabove. A column may comprise one or several beds containing chromatographic media. Those feed tanks, filters, piping connecting flow between columns and/or beds where so connected, pumps, valving, pressure regulators, metering equipment, flow control and microprocessor equipment utilized in the embodiment are well known in construction and function to those of ordinary skill in the art.

Water, preferably deionized water which is essentially free of dissolved ions, preferably with ionic conductivity of 8-10 μS/cm and which is essentially free of other organic solvents is used as the mobile phase stream for the SMB zone.

Decolorization

Decolorization of the extract stream from the SMB zone in one embodiment can be carried out by evaporating the extract stream to a Brix of 25 to 35 and passing the evaporated extract stream to a decolorization zone. In the decolorization zone, the evaporated extract stream is contacted with an absorbent such as activated carbon to remove color agents from the evaporated extract stream to provide a decolorized extract stream. The decolorization zone can process either evaporated SMB extract or dilute SMB extract (not-evaporated having a Brix of about 3 to 6). The following table provides an indication of the efficiency of the color removal zone of the present invention:

| Streams | Sugar Brix | Absorbance Value at 420 nm | Equivalent ICUMSA* Index |
|---|---|---|---|
| Feed to SMB | 14.5 | 3.8-4.2 | 3900-4200 |
| Dilute extract from SMB zone | 3-4.5 | 0.3-0.5 | 1600 |
| Dilute decolorized effluent | 3-4.5 | 0.03 | 5-7 |
| Evaporated extract | 30 | 3.0-3.5 | 5000 |
| Decolorized evaporated extract | 25-35 | 0.3-0.5 | 15-25 |
| SMB Primary Raffinate | 2.5 | 1.5-2.0 | 2500 |

The ICUMSA (International Commission for Uniform Methods of Sugar Analysis) index value for very highly pure sugar for use in medicinal chemistry for human consumption is ICUMSA 45 or lower. Thus, the ICUMSA value of the decolorized stream should range from about 15 to 25 in order to provide a final crystalline mannose product having an ICUMSA index value of less than 45.

Desalination

Desalination of the decolorized stream was performed in a desalination zone which comprised two resin zones connected in series, wherein the first resin zone contained an anion exchange resin, and the second resin zone contained a cation exchange resin. Following the activation of the first resin zone with a dilute basic solution such as 0.1 N NaOH, and the activation of the second resin zone with a dilute acid solution such as 1% HCl, the decolorized stream was passed to the desalination zone. The eluent from the first resin zone was passed to the second resin zone to provide the desalinized stream. When the desalination efficiency fell below a desired level, the first and second resin zones were regenerated or replaced. Regeneration of the anion exchange resin was carried out by passing an effective amount of dilute basic solution through the first resin zone. In a similar manner, the cation exchange resin in the second resin zone was regenerated by passing an effective amount of a dilute acid solution through the second resin zone. The desalination zone can contain a plurality of beds containing both anion exchange resin and cation exchange resin and configured in any manner to allow the batch or continuous processing of the SMB extract stream. A resin zone may comprise one or several chambers or beds containing the anion exchange or cation exchange resin media. Those feed tanks, filters, piping connecting flow between resin zones and/or beds where so connected, pumps, valving, pressure regulators, metering equipment, flow control and microprocessor equipment utilized in the embodiment are well known in construction and function to those of ordinary skill in the art.

Crystallization

In one embodiment of the present invention, the desalinized stream was evaporated under vacuum conditions (−25 mm of Hg and at 60° C.) to a sugar concentration greater than about 90 Brix, or about a 90-95 Brix range. At this sugar concentration, the evaporated stream forms a sugar syrup. A portion of acetic acid (>99.7% ACS grade) equal in weight to the weight of the sugar syrup was warmed to a temperature of about 45-55° C. and added to the sugar syrup to form a sugar/acetic acid mixture. In order to initiate crystallization or nucleation, a nucleation portion of pure crystalline Mannose (>99% pure) was added to the sugar/acetic acid mixture. The sugar/acetic acid mixture was stirred continuously until homogeneous, and then the sugar/acetic acid mixture was allowed to settle for about 10 to 18 hours at about room temperature (20-25° C.). After about 12 hours the sugar/acetic acid mixture was cooled in a cooling step to a crystallization temperature of less than 10° C., and more particularly the sugar/acetic acid mixture was cooled in a cooling step to a crystallization temperature of about 5-7° C. and retained at that crystallization temperature until pure d-mannose crystals formed. Pure d-mannose crystals started to form about 24 hrs after the cooling step. The sugar/acetic acid mixture containing the d-mannose crystals was filtered at the crystallization temperature using 0.45 micron filter and the d-mannose crystals were retained. The retained d-mannose crystals were washed with cold ethanol (ACS grade at a temperature of about 5-10 deg C.) and the recovered d-mannose crystals were vacuum dried to provide the pure d-mannose crystals having a purity of greater than 95 wt-% d-mannose, and more particularly, to provide the pure d-mannose crystals having a purity of greater than 99 wt-% d-mannose.

Mannose Precipitation

In a further embodiment of the present invention, as alternative to crystallization as described herein above, the desalinized stream was evaporated under vacuum conditions (−25 mm of Hg and at 60° C.) to a sugar concentration greater than about 90 Brix, or about a 90-95 Brix range to provide the second evaporization stream. At this sugar concentration, the second evaporation stream forms a sugar syrup. An equivalent amount of ethanol (99 wt-% ACS grade) equal in weight to the sugar syrup was added at 55-60° C. to the sugar syrup to form a sugar syrup/ethanol mixture, and instantaneously, white solids began to precipitate in the sugar syrup/ethanol mixture. The temperature of the sugar syrup/ethanol mixture was slowly lowered from 50-60° C. to about 30-35° C. while mixture was continuously stirred. The stirring was stopped and mixture was kept still for about 30 min at about a temperature of about 10 to about 12° C. The supernatant ethanol was then decanted off leaving a white hardened precipitate. The white hardened precipitate was transferred an evaporator while maintained at an evaporation temperature of 15-25° C. and −25 mm of Hg vacuum to evaporate residual ethanol and provide small solid granules. The evaporation was continued at 15-25° C. and −25 mm of Hg vacuum to dry the solid granules until white fine powder-like granules were formed having a purity of equal to or greater than 95 wt-% d-mannose.

The following examples are provided to illustrate the present invention. These examples are shown for illustrative purposes, and any invention embodied therein should not be limited thereto.

EXAMPLES

All purities or recovery values are generally expressed in terms of the total sugar content of the product or stream. In general, a high purity stream will comprise from 90 to 99 wt-% of the key component based on the total sugar in the product or stream. Similarly, recoveries are expressed in terms of recovery based on the total sugar content.

Example 1

A chromatographic column of 316 stainless steel and having an inside diameter of 10 mm and a length of 250 mm was prepared for use in establishing the elution profile of the major components of a palm oil kernel sugar mixture. The chromatographic column was filled with 14 g of DOWEX 99CA/320 (Available from the Dow Chemical Company, Midland, Mich.), a strong acid cation exchange resin in calcium form as a stationary phase. The resin particles were in the form of beads and were 320 microns in size. A flow of mobile phase desorbent as deionized water at a rate of 0.5 ml/min was established in the column at a temperature of 60-65° C. 1 ml feed mixture of about 14.5 Brix obtained from palm oil kernel cake enzyme treatment (composition as described hereinabove) was injected into the column and the resulting eluent fractions were collected at 4 minute intervals. The eluent from the chromatographic column was monitored by refractive index using a Waters 410 RI detector (Available from Waters Corporation, Milford Mass.). The fractions were analyzed by HPLC. The results of Experiment were used to calculate relative selectivity's of mannose with respect to other sugars. The relative selectivity was determined by considering the retention times or volumes of each of the components and the void volume of the column. The column void time was determined by injecting a non-adsorbing solution of calcium chloride and detecting its elution time.

|  | Elution volume, ml | Selectivity (alpha) |
|---|---|---|
| Glucose | 16 | 2.74 |
| Xylose | 15.5 | 3.07 |
| Galactose | 20 | 1.47 |
| Mannose | 24 | 1.0 |
| Arabinose | 28 | 1.32 |

Therefore, it was determined that a d-mannose separation in a simulated moving bed SMB process was feasible because the selectivity of the d-mannose separation over the strong acid cation exchange resin stationary phase was greater than 1.3 with respect to all other sugars.

Example 2

Simulated Moving Bed Technology—D-Mannose-SMB Separation

An OCTAVE 300 lab scale SMB unit (Available from Semba Biosciences, Madison, Wis.) that contained a complex valve unit and 4 isocratic pumps (0-300 ml/min capacity) was used to simulate the SMB operation. The SMB system had 8 valve ports. Eight columns of 316 stainless steel, wherein each column had an inside diameter of 22 mm and a length of 300 mm, were connected in a stationary configuration and the valve switches were operated by pneumatic pressure (of about 320 psi/2206 kPa) to function in the same manner as a rotary valve. The ends of each of the columns were protected by 20 μm PTFE frits. Each column was filled with about 90 grams of DOWEX monosphere 99CA/320 (Available from Dow Chemical Company, Midland, Mich.), a strong acid cation calcium exchange resin stationary phase. Flow rates were controlled through control panel by adjusting valves and pump rates. The circuit was divided into 4 different zones, i.e. (2-3-2-1) configuration. Zone 1 consisted of 2 columns between desorbent entry point and extract withdrawal point (desorption zone). Zone 2 contained 3 columns between extract withdrawal point and feed introduction point (rectification zone). Zone 3 was an adsorption zone consisting of 2 columns between feed inlet and primary raffinate withdrawal point. Zone 4 was a concentration zone for raffinate which provided part of the clear desorbent for recycle. The desorbent was water at temperature 60-65 deg C.

The average SMB operating conditions can be summarized as follows:

| Stream | Flow rate, ml/min |
|---|---|
| Feed | 2.0 |
| Desorbent | 15.8 |
| Extract | 5.8 |
| Primary raffinate | 4.0 |
| Secondary raffinate | 8.0 |
| Step time/switch time | 360 sec |

The average feedstream to the SMB zone had a density of 14.5 Brix with the following composition:

| Components | Value | Units |
|---|---|---|
| Glucose | 1.192 | Wt % |
| Xylose | 0.055 | Wt % |
| Galactose | 0.122 | Wt % |
| Arabinose | 0.57 | Wt % |
| Mannose | 8.455 | Wt % |
| Total Sugars | 14.5 | Wt-% |
| Phenolic compounds | 855.7 | GAE/L |
| Proteins/Biomass | 465.8 | μg/L |
| Conductivity | 4.57 | mS/cm |
| pH range | 4.0-4.5 | |

The average feedstream to the SMB unit contained salt ions as shown hereinbelow:

| Ions | ppm |
|---|---|
| Calcium | 207 |
| Chloride | 245 |
| Fluoride | <0.05 |
| Magnesium | 706 |
| Nitrate | 4.76 |
| Phosphate | 154 |
| Potassium | 1447 |
| Sodium | 21.5 |
| Sulfate | 280 |

The average composition of the extract stream withdrawn from the SMB is shown hereinbelow:

| Components |  | wt % |
|---|---|---|
| Glucose | 0.03 | wt % |
| Xylose | 0.05 | wt % |
| Galactose | 0.005 | wt % |
| Arabinose | 0.226 | wt % |
| Mannose | 3.18 | wt % |
| Total Sugars | 4.40 | wt % |
| Phenolic compounds | ND | GAE/L |
| Proteins | ND | μg/L |
| Conductivity | 2.0-2.5 | mS/cm |
| pH range | 5.5-6.0 | |

ND—None Detectable
mS/cm (milli-Siemens)

The composition of the primary raffinate stream withdrawn from the SMB is shown hereinbelow:

| Composition |  | wt % |
|---|---|---|
| Glucose | 0.685 | wt % |
| Xylose | 0.032 | wt % |
| Galactose | 0.070 | wt % |
| Arabinose | 0.000 | wt % |
| Mannose | 0.243 | wt % |
| Total Sugars | 2.53 | wt-% |

-continued

| Composition | | wt % |
|---|---|---|
| Phenolic compounds | 492.02 | GAE/L |
| Proteins | 267.83 | µg/L |
| Conductivity | 3.0-3.5 | mS/cm |
| pH range | 4.0-4.5 | |

The SMB plant was run continuously for a period of 3 weeks. During the run, the purity of the d-mannose in the extract averaged about 99 wt % with respect to the glucose in the feed, and the purity based on the total sugar in the extract was greater than or equal to 95 wt %. The process recovery of d-mannose in extract was greater than or equal to 95% based on the total sugar in the feed.

Example 3

Desalination of Decolorized Extract from the SMB Zone 2 columns of 316 stainless steel, each 22 mm in diameter and 300 mm in length and capped by 20 µm frits were packed with about 98 grams of resin. The first column, or anion exchange column, was packed with a strong anion exchange resin, DOWEX 1×8 200-400 MESH Cl (styrene-DVB gel with 8% cross linkage) (Available from Dow Chemical Company, Midland, Mich.) and the second column, or cation exchange column, was packed with 98 grams of a strong cation exchange resin, DOWEX 50WX4-400 (styrene-DVB gel with 4% cross linkage) (Available from Dow Chemical Company, Midland, Mich.).

The anion exchange column was ion exchanged by passing about 300 mL or about 10 bed volumes of 0.1 M solution of NaOH in deionized water through the anion exchange resin to convert the resin to the hydroxyl form (—OH) in the first column, and the cation exchange column was activated by passing 1% solution of dilute HCl acid in deionized water to activate the cation exchange resin (hydrogen form +H) in the cation exchange column. Both the anion and the cation exchange columns were then thoroughly washed with 5 bed volumes of deionized water, separately.

Ionic conductivities of all sugar solutions were measured using an Oakton CON6 Acorn Series conductivity meter (Available from Oakton Instruments, Vernon Hills, Ill.). According to the desalination process of the present invention, each SMB extract stream was passed through cation exchange resin column first using a 100 ml capacity pump at 25 ml/min flow rate, and the effluent from the cation exchange resin column was then passed through the anion exchange resin column. The eluent from each column was continuously monitored using conductivity measurements. The desired conductivity following the cation exchange was about 200-300 µS/cm for the dilute extract stream, and about 10-15-mS/cm for the concentrated extract stream. The conductivity of the SMB extract stream following the anion exchange resin column is expected to be less than 40-50 µS/cm in both the cases.

The dilute SMB extract stream following decolorization had following sugar composition:

| Sugars | Value | wt % |
|---|---|---|
| Glucose | 0.03 | wt % |
| Xylose | 0.05 | wt % |
| Galactose | 0.005 | wt % |
| Arabinose | 0.226 | wt % |
| Mannose | 3.18 | wt % |
| Total | 4.49 | wt % |
| Phenolic compounds | ND | GAE/L* |
| Proteins | ND | µg/L |
| Conductivity | 2.0.-2.5 | mS/cm |
| pH range | 5.5-6 | |

*Gallic Acid Equivalent (GAE)/L

Approximate ionic distribution of Inlet dilute extract from SMB, after cation exchange bed and after anion exchange bed is as follows. (in ppm-wt)

| Ion type | Extract Before Exchange | After Cation exchange | After anion exchange |
|---|---|---|---|
| Calcium | 82.1 | 1.00 | 1.00 |
| Chloride | 97.2 | 97.2 | 2.00 |
| Fluoride | 0.02 | 0.02 | 0.00 |
| Magnesium | 280.0 | 2.00 | 2.00 |
| Nitrate | 1.89 | 1.89 | 0.00 |
| Phosphate | 61.1 | 61.1 | 1.00 |
| Potassium | 573.8 | 3.00 | 3.00 |
| Sodium | 8.53 | 0.00 | 0.00 |
| Sulfate | 111.0 | 111.0 | 0.00 |
| Total ppm-wt | 1215.55 | 277.17 | 9.00 |

When the eluent started exhibiting higher conductivities than desired, the resin was assumed to be exhausted and was either regenerated or replaced. Regeneration of the resin in the desalination process comprised passing about 10 bed volumes of 0.1 M NaOH solution in deionized water through the anion exchange resin (hydroxyl form —OH), and passing a 1% dilute HCl acid solution in deionized water through the cation exchange resin (hydrogen form +H). After regeneration of the anion and cation columns, both columns were washed with 5 bed volumes of deionized water before placing them back in service in the desalination process.

Extract from SMB was concentrated by evaporation to about 30 Brix, and over the run ranged from about 25 to about 35 Brix, and had following composition:

| Sugars Total | 25-35 Brix | wt % |
|---|---|---|
| Glucose | 0.3 | wt % |
| Xylose | 0.5 | wt % |
| Galactose | 0.05 | wt % |
| Arabinose | 2.26 | wt % |
| Mannose | 31.8 | wt % |
| Total | 34.91 | wt-% |
| Phenolic compounds | ND | GAE/L* |
| Proteins | ND | µg/L |
| Conductivity | 25-35 | mS/cm |
| pH range | 5-5.5 | |

*Gallic Acid Equivalent (GAE)/L
mS/cm (milli-Siemens)

The concentrated extract was passed through the above described desalination process comprising the cation exchange column and then anion exchange column. The inlet and outlet salt distribution was as follows:

| Ion type | Conc. Extract Before | After Cation exchange | After anion exchange |
|---|---|---|---|
| Calcium | 820 | 10.00 | 10.00 |
| Chloride | 971 | 971.00 | 3.00 |
| Fluoride | 0.20 | 0.20 | 0.00 |
| Magnesium | 2799 | 20.00 | 20.00 |
| Nitrate | 18.8 | 18.90 | 0.00 |
| Phosphate | 610 | 617.00 | 3.00 |
| Potassium | 5738 | 20.00 | 2.00 |
| Sodium | 85 | 1.00 | 1.00 |
| Sulfate | 1110 | 1111.00 | 5.00 |
| Total ppm | 12155 | 2769.10 | 44.00 |

(Note: All values in ppm-wt)

Example 4

Color Agent Determination

The presence of color agents in the SMB complex streams was determined as a color absorbance value which was measured at 420 nm absorbance wavelength in terms of optical density of the solution using a SPECTRAMAX PLUS spectrometer (Available from Molecular Devices, LLC of Sunnyvale, Calif.). The optical density or absorbance of the filtered feed to the SMB was found to be about 4.0. The optical density or absorbance of the extract stream produced by the SMB zone ranged from 0.3 to 0.5, and the optical density of the primary raffinate stream from the SMB zone ranged from 1.5 to 2.0.

Example 5

Color Agent Removal

According to the process of one embodiment of the invention, the extract stream from the SMB zone (See Example 2.) was evaporated to provide an evaporated extract stream having a sugar content of about 30 Brix (suitable range 25-35 Brix) using vacuum rotary evaporator with a Buchi ROTOVAPOR, R-210 (Available from Buchi Corporation, New Castle, Del.). The optical density of the evaporated extract stream before decolorization ranged between 3.0-3.5. A 316-stainless steel column, or decolorization column, having a length of 300 mm and an inside diameter of 22 mm was packed with 80 grams of 80×325 mesh TOG activated carbon adsorbent (Available from Calgon Carbon Corporation, Pittsburgh, Pa.). The column was flushed with deionized water having a conductivity of 8-10 µS/m to remove any fine carbon particles. The dilute extract stream at a temperature of 25° C. was passed continuously through the decolorization column. A 100 capacity pump was used for this operation and the flow rate was maintained at 25 ml/min. The decolorization column effluent, or decolorized stream was collected from the decolorization column until the absorbance value of eluent increased from null to less than or equal to 0.2, or after passing about 950-1000 ml of concentrated extract.

Example 6

Continuous Decolorization of Highly Pure Mannose Stream

A decolorization column having an inside diameter of 22 mm and a length of 300 mm and constructed of 316 stainless steel and filled with 80 grams of TOG 80×325 activated carbon adsorbent (See above.) was installed in series with the SMB zone by allowing the extract stream or highly pure mannose stream from the SMB zone to pass directly to the decolorization column. The highly pure mannose stream was of the composition of Example 2, having about 4.49 Brix, 2.5 mS/cm conductivity at 25° C., and an optical density of between 0.3 and 0.5. The extract SMB flow rate was 5.8 ml/min. The carbon column was assumed to be saturated and replaced after the eluent of the decolorization zone reached an absorbance value greater than or equal to 0.03. The effluent absorbance reached 0.03 after about 20-21 hrs on stream, or after passing about 7500 ml of SMB extract.

Example 7

Crystallization of D-Mannose from Evaporated Extract Syrup 300 grams of decolorized and desalted evaporated extract at about 30 Brix (between about 25-35 Brix) from the continuous run of the SMB in Example 2 was evaporated under vacuum conditions (−25 mm of Hg and at 60° C.) to a sugar concentration greater than about 90 Brix, or about a 90-95 Brix range, which corresponded to a point where the weight of the decolorized and desalted evaporated extract remaining was about 100 grams and formed a sugar syrup. A 100 gms portion of acetic acid (>99.7% ACS grade) was warmed to a temperature of 50° C. and added to the sugar syrup to form a sugar/acetic acid mixture. In order to initiate crystallization or nucleation, about 20 mg of pure crystalline Mannose (>99% pure) was added to the sugar/acetic acid mixture. The sugar/acetic acid mixture was stirred continuously until homogeneous, and then the mixture was allowed to settle for about 12 hours at room temperature (25° C.). After 12 hours the sugar/acetic acid mixture was cooled in a cooling step to a crystallization temperature of less than 10° C. and more particularly about 5-7° C. and retained at that crystallization temperature. Pure d-mannose crystals started to form about 24 hrs after the cooling step. The sugar/acetic acid mixture containing the d-mannose crystals was filtered at the crystallization temperature using 0.45 micron filter and the d-mannose crystals were retained. The retained d-mannose crystals were washed with cold ethanol (ACS grade at a temperature of about 5-10 deg C.) and the d-mannose crystals were vacuum dried and analyzed on HPLC for purity.

Extract Analysis Before Crystallization (Following Concentration to 90 Brix)

| Sugars | Value | wt % |
|---|---|---|
| Glucose | 0.78 | wt % |
| Xylose | 1.3 | wt % |
| Galactose | 0.13 | wt % |
| Arabinose | 5.876 | wt % |
| Mannose | 82.68 | wt % |
| Total | 90.64 | wt % |
| Phenolic compounds | ND | GAE/L |
| Proteins | ND | µg/L |
| Conductivity | 20-30 | µS/cm |
| pH range | 7 | |

µS/cm—(micro-Siemens)

Recovered d-Mannose Crystals Analysis (Dry)

| Sugars | Wt-% |
| --- | --- |
| Glucose | 0.1 |
| Xylose | 0.1 |
| Galactose | 0.1 |
| Arabinose | 0.6 |
| Mannose | 99.1 |
| Total | 100.0 |

The purity of d-mannose crystals was found to be greater than or equal to 99 wt % and the wt. of d-mannose crystals recovered was about 65-70 grams. Thus, the overall yield of d-mannose crystal was found to be 80-85 wt % for samples obtained over from the continuous run of the SMB disclosed herein above in Example 2.

Example 8

Ethanol Precipitation of Concentrated D-Mannose Extract 300 grams of the evaporated highly pure mannose stream having a Brix value of 25-35, from the continuous run of the SMB in Example 2 was concentrated to syrup using a rotary evaporator (Buchi ROTOVAPOR, R-153(Available from Buchi Corporation, New Castle, Del.) at 60° C. temperature and the vacuum at −25 mm of Hg. After the solution was concentrated to form a sugar syrup of about 90 Brix or about reduced to a weight of about 100 gms, an equivalent amount (100 grams) of ethanol (ACS grade) was added at 60° C. to the sugar syrup to form a sugar syrup/ethanol mixture, and instantaneously, white solids began to precipitate in the sugar syrup/ethanol mixture. The temperature of the sugar syrup/ethanol mixture was slowly lowered from 60° C. to 30° C. while mixture was continuously stirred. The stirring was stopped and mixture was kept still for about 30 min at about a temperature of 10° C. The supernatant ethanol was then decanted off leaving a white hardened precipitate. The white hardened precipitate was transferred to a rotary evaporator maintained at 15-25° C. and −25 mm of Hg vacuum to evaporate residual ethanol and form small solid granules. The evaporation was continued at 15-25° C. and −25 mm of Hg vacuum to dry the solid granules until white fine powder-like granules were formed. The granules were tested for purity using HPLC method.

Extract Analysis Before Ethanol Precipitation:

| Sugars | Value | wt % |
| --- | --- | --- |
| Glucose | 0.78 | wt % |
| Xylose | 1.3 | wt % |
| Galactose | 0.13 | wt % |
| Arabinose | 5.876 | wt % |
| Mannose | 82.68 | wt % |
| Total | 90.6 | wt % |
| Phenolic compounds | ND | GAE/L |
| Proteins | ND | µg/L |
| Conductivity | 20-30 | µS/cm |
| pH range | 6.5-7 | |

Mannose Precipitate Analysis: (White Dry Fine Granules)

| Sugars | wt-% |
| --- | --- |
| Glucose | 0.25 |
| Xylose | 0.15 |
| Galactose | 0.11 |
| Arabinose | 2.3 |
| Mannose | 97.19 |
| Total | 100.0 |

The dried mannose granules were weighed about 74-78 grams. The purity of mannose granules using HPLC method was found to be about 97 wt % and precipitation yield was about 90-95%.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims, while the description, abstract and drawings are not to be used to limit the scope of the invention. The invention is specifically intended to be as broad as the claims below and their equivalents.

We claim:

1. A process for the production of a high purity d-mannose product from fermented palm oil kernel meal using simulated moving bed separation, said process comprising:
   a. passing a palm kernel meal stream comprising water, d-mannose, d-glucose, other sugars, color agents, salts and biomass at a pH of between about 5 and 7 to a filtration zone comprising a filter media effective to remove at least a portion of the biomass to provide a filtered feedstream comprising water, d-mannose, d-glucose, salts, other sugars, and color agents:
   b. passing the filtered feedstream to a simulated moving bed (SMB) zone to provide a highly pure mannose extract stream comprising d-mannose, color agents, salts and water and a primary raffinate stream comprising water, d-glucose, salts, and other sugars, and a secondary raffinate stream consisting essentially of water, said SMB zone comprising a plurality of adsorption beds containing a stationary phase agent comprising a strong acid cation exchange resin in which exchange sites are a metal selected from the group consisting of $Ca^{2+}$, $Na^+$ and $K^+$, and introducing a mobile phase stream consisting of water to said SMB zone, said SMB zone being operated at effective conditions and an effective SMB cycle to provide a continuous process for producing the highly pure mannose stream and the secondary raffinate stream and returning at least a portion of the secondary raffinate stream to the SMB zone to be admixed with the mobile phase stream;
   c. passing the highly pure mannose stream to a decolorization zone wherein the highly pure mannose extract stream is contacted with a medium effective to at least partially remove the color agents to provide a decolorized stream comprising d-mannose, salts and water;
   d. passing the decolorized stream to a first evaporation zone to remove at least a portion of the water and provide a first evaporated stream;

e. passing the first evaporated stream to a desalination zone to provide a desalinized stream;

f. passing the desalinized stream to a second evaporation zone to provide an evaporated desalinized stream;

g. passing the evaporated desalinated extract stream to a precipitation zone or a crystallization zone to provide wet mannose crystals; and, h. passing the wet mannose crystal stream to a vacuum drying zone to provide the high purity d-mannose product.

2. The process of claim 1, wherein the plurality of adsorption beds is 8 and the effective SMB cycle comprises a 2-3-2-1 SMB cycle.

3. The process of claim 1, wherein the effective conditions for the operation of the SMB zone include a temperature of from about 50 to about 65° C.

4. The process of claim 1, wherein the the exchange sites are calcium.

5. The process of claim 1, wherein the filter media is a membrane having at least a 10 Da molecular weight cut off to remove at least a portion of the biomass.

6. The process of claim 1, wherein the medium effective to at least partially remove the color agents is an adsorbent or absorbent comprising activated carbon.

7. The process of claim 1, wherein the decolorized stream comprises an optical density or absorbance less than or equal to 0.2.

8. The process of claim 1, wherein the first evaporization zone provides a first evaporated stream having a Brix value of from about 25 to about 30 Brix.

9. The process of claim 1, wherein the feedstream comprises from about 35 to about 70 wt-% d-mannose relative to the total sugar in the feedstream.

10. The process of claim 1, wherein the desalinized zone comprises two resin zones connected in series, wherein the first resin zone comprises an anion exchange resin, and the second resin zone comprises a cation exchange resin and the first evaporated stream is passed to the first resin zone to provide a desalting eluent and the desalting eluent is passed to the second resin zone to provide the desalinized stream.

11. The process of claim 1, wherein the high purity d-mannose product comprises from 95 to about 99.9 wt-% d-mannose.

12. The process of claim 1, wherein the high purity d-mannose product is a solid in the form of a powder or a crystal.

13. The process of claim 1, wherein the highly pure mannose extract stream comprises more than about 95 wt-% d-mannose with respect to the total sugar in the highly pure mannose extract stream.

14. The process of claim 1, wherein the crystallization zone further comprises the steps of admixing the evaporated desalinized stream with acetic acid, nucleating the admixture, maintaining the admixture at effective crystallization conditions, cooling, filtering and recovering retained d-mannose crystals and washing the retained d-mannose crystals with ethanol to provide the wet mannose crystals.

15. The process of claim 13, wherein the effective crystallization conditions include a crystallization temperature of less than about 10° C.

16. The process of claim 1, wherein the precipitation zone further comprises the steps of contacting the evaporated desalinated stream with ethanol at effective precipitation conditions, recovering wet mannose crystals.

17. The process of claim 1, wherein filtered feedstream comprises less than about 0.5 wt-% biomass.

18. A process for the production of a high purity d-mannose product from fermented palm oil kernel meal using simulated moving bed separation, said process comprising:

a. passing a palm kernel meal stream comprising water, d-mannose, d-glucose, other sugars, color agents, salts and biomass at a pH of between about 5 and 7 to a filtration zone comprising a filter media effective to remove at least a portion of the biomass to provide a filtered feedstream comprising water, d-mannose, d-glucose, salts, other sugars, and color agents:

b. passing the filtered feedstream to a simulated moving bed (SMB) zone to provide a highly pure mannose extract stream comprising d-mannose, color agents, salts and water and a primary raffinate stream comprising water, d-glucose, salts, and other sugars, and a secondary raffinate stream consisting essentially of water, said SMB zone comprising a plurality of adsorption beds containing a stationary phase agent comprising a strong acid calcium cation exchange resin, and introducing a mobile phase stream consisting of water to said SMB zone, said SMB zone being operated at effective conditions and being operated in an effective SMB cycle to provide a continuous process for producing the highly pure mannose stream and the secondary raffinate stream and returning at least a portion of the secondary raffinate stream to the SMB zone to be admixed with the mobile phase stream;

c. passing the highly pure mannose stream to a decolorization zone wherein the highly pure mannose stream is contacted with a medium effective to at least partially remove the color agents to provide a decolorized extract stream comprising d-mannose, salts and water;

d. passing the decolorized stream to a first evaporation zone to remove at least a portion of the water and provide a first evaporation stream;

e. passing the first evaporation stream to a desalination zone to provide a desalinized stream;

f. passing the desalinized stream to a second evaporation zone to provide a second evaporated stream;

g. passing the second evaporated stream to a precipitation zone or a crystallization zone to provide wet mannose crystals; and, h. passing the wet mannose crystal stream to a vacuum drying zone to provide the high purity d-mannose product.

19. The process of claim 18, wherein the second evaporation stream is passed to a precipitation zone comprising the steps of contacting the second evaporation stream with ethanol at effective precipitation conditions including a precipitation temperature of from about 10° C. to about 60° C. and recovering wet mannose crystals to provide wet mannose crystals.

20. A simulated moving bed separation process for the production of a high purity d-mannose extract stream from fermented palm oil kernel meal using simulated moving bed separation, said process comprising passing a palm kernel meal stream comprising water, d-mannose, d-glucose, other sugars, color agents, biomass and salts at a pH of between about 5 and 7 to a simulated moving bed (SMB) zone to provide a highly pure mannose stream comprising d-mannose, color agents, salts, biomass, and water and a primary raffinate stream comprising water, d-glucose, salts, and other sugars, and a secondary raffinate stream consisting essentially of water, said SMB zone comprising a plurality of adsorption beds containing a stationary phase agent comprising a strong acid cation exchange resin in which exchange sites are $Ca^{2+}$, and introducing a mobile phase stream containing water to said SMB zone, said SMB zone being operated at effective conditions to provide a continuous process for producing the highly pure mannose stream comprising greater than about 95 wt-% d-mannose based on the total sugar in the highly pure mannose stream and returning at least a portion of the secondary raffinate stream to the SMB zone to be admixed with the mobile phase stream, and subsequently removing the biomass from the highly pure mannose stream.

\* \* \* \* \*